United States Patent
Serlie et al.

(10) Patent No.: US 9,311,717 B2
(45) Date of Patent: Apr. 12, 2016

(54) PROCESSING AND DISPLAYING A BREAST IMAGE WITH OVERLAID GLANDULAR CONTOUR

(71) Applicant: KONINKLIJKE PHILIPS N.V., Eindhoven (NL)

(72) Inventors: Iwo Willem Oscar Serlie, Noord Brabant (NL); Rudolph Martherus, Vlissingen (NL)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 14/368,068

(22) PCT Filed: Dec. 6, 2012

(86) PCT No.: PCT/IB2012/057025
§ 371 (c)(1),
(2) Date: Jun. 23, 2014

(87) PCT Pub. No.: WO2013/093687
PCT Pub. Date: Jun. 27, 2013

(65) Prior Publication Data
US 2015/0003702 A1      Jan. 1, 2015

Related U.S. Application Data

(60) Provisional application No. 61/578,956, filed on Dec. 22, 2011.

(51) Int. Cl.
*G06K 9/00* (2006.01)
*G06T 7/00* (2006.01)
(Continued)

(52) U.S. Cl.
CPC ............. *G06T 7/0083* (2013.01); *A61B 5/7275* (2013.01); *A61B 6/502* (2013.01); *G06T 7/0012* (2013.01); *G09G 5/14* (2013.01); *G06T 2207/10116* (2013.01); *G06T 2207/20124* (2013.01); *G06T 2207/30068* (2013.01); *G09G 2340/12* (2013.01)

(58) Field of Classification Search
None
See application file for complete search history.

(56) References Cited

U.S. PATENT DOCUMENTS 5,133,020 A    7/1992  Giger et al.
5,825,910 A *  10/1998 Vafai ............................ 382/132
(Continued)

FOREIGN PATENT DOCUMENTS

WO       2006018816 A2    2/2006

OTHER PUBLICATIONS

Tabar, Laszlo et al. "Breast cancer: the art and science of early detection with mammography: perception, interpretation, histopathologic correlation", 2005.
(Continued)

*Primary Examiner* — Tahmina Ansari

(57) ABSTRACT

A system for processing a breast image is described. A glandular tissue contour detector (1) is arranged for detecting a contour (407) of a glandular tissue (303) represented in the breast image (310), the glandular tissue detector (1) detecting the contour of a region within the image that comprises the mammary glands of a breast (301) represented in the breast image (310).The glandular tissue contour detector (1) comprises a concave hull determiner (2) for determining a concave hull of the region to obtain the contour (407).A display unit (3) is arranged for displaying the breast image (310) with the contour (407) superimposed.

20 Claims, 3 Drawing Sheets

(51) Int. Cl.
*A61B 5/00* (2006.01)
*A61B 6/00* (2006.01)
*G09G 5/14* (2006.01)

(56) References Cited

U.S. PATENT DOCUMENTS

| | | | | |
|---|---|---|---|---|
| 6,630,937 | B2* | 10/2003 | Kallergi et al. | 345/619 |
| 2005/0135664 | A1* | 6/2005 | Kaufhold et al. | 382/131 |
| 2009/0220139 | A1 | 9/2009 | Schneider et al. | |
| 2009/0274354 | A1* | 11/2009 | Ng et al. | 382/131 |
| 2011/0243418 | A1 | 10/2011 | Sugiura | |
| 2015/0003702 | A1* | 1/2015 | Serlie et al. | 382/128 |

OTHER PUBLICATIONS

Tang, J. et al. "Computer-Aided Detection and Diagnosis of Breast Cancer With Mammography: Recent Advances", IEEE Transactions on Information Technology in Biomedicine, vol. 13, No. 2 Mar. 2009, pp. 236-251.

Tzkopoulos, S.D. et al: "A fully automated scheme for mammographic segmentation and classification based on breast density and asymmetry", Computer Methods and programs in Biomedicine, Elsevier, Amsterdam, NL, vol. 102, No. 1, Nov. 30, 2010, pp. 47-63.

Ferrari R.J. et al.: "Analysis of Asymmetry in Mammograms via Directional Filtering with Gabor Wavelets", IEEE Transactions on Medical Imaging, IEEE Service Center, Piscataway, NJ, US, vol. 20, No. 9, 2001.

Matsubara, T. et al. "Novel method for detecting mammographic distortion based on concentration of mammary gland". International Congress Series, vol. 1268, Jun. 2004, pp. 867-871.

Van Engeland, S. et al. "A Comparison of Methods for Mammogram Registration". IEEE Transactions of Medical Imaging, vol. 22, No. 11, Nov. 2003.

IHE Radiology: Mammography User's Handbook, ACC, HIMSS, RSNA, http://www.ihe.net/resources/handbook.cfm.

* cited by examiner

PROCESSING AND DISPLAYING A BREAST IMAGE WITH OVERLAID GLANDULAR CONTOUR

This application is a national stage application under 35 U.S.C. §371 of International Application No. PCT/IB2012/057025 filed on Dec. 6, 2012 and published in the English language on Jun. 27, 2013 as International Publication No. WO/2013/093687, which claims priority to U.S. Application No. 61/578,956 filed on Dec. 22, 2011, the entire disclosures of which are incorporated herein by reference.

FIELD OF THE INVENTION

The invention relates to processing a breast image. The invention further relates to displaying a breast image.

BACKGROUND OF THE INVENTION

It is known to diagnose diseases of the breast by visual inspection of mammograms. To display the area of interest, panning and zooming is commonly used. To best assess differences in density, viewing parameters are used to fine-tune the display. For example, window width and window level are used to best use the different shades of gray that are available. One aspect of the analysis of images by the health professional includes the assessment of symmetry of the left and right breast. This may be achieved by display of a pair of breast images, one next to the other. Also, similarity between breast images of the same breast acquired at different moments in time can be assessed in order to arrive at a diagnosis.

The assessment of breast images may include the detection of lesions. The assessment may also include the assessment of the overall shape or appearance of the glandular tissue. This overall shape or appearance may be referred to hereinafter as breast architecture. Architectural distortion is defined in the Breast Imaging Reporting and Data System (BI-RADS) as follows: "The normal architecture (of the breast) is distorted with no definite mass visible. This includes spiculations radiating from a point and focal retraction or distortion at the edge of the parenchyma. Architectural distortion can also be an associated finding."

In clinical practice, mammograms are often examined in pairs, using the natural symmetry to visually detect abnormalities by detecting asymmetry of glandular tissue of the left and right breast as seen in mammograms. "Breast cancer: the art and science of early detection with mammography: perception, interpretation, histopathologic correlation", by László Tabár et al., Thieme, 2005, discloses that parenchymal contour change is a sign that may lead to the detection of small invasive tumors without calcification. Screening mammograms tend to be read in batches, with the average time spent for negative cases being about 15 seconds and positive cases about 1 minute, including dictation. The vast majority of screening cases are negative. The task of examining the natural symmetry of mammography image pairs involves a mental effort to compare the shape of the left and right breasts for irregularities. In the field of digital mammography, there is a need for simple and well-designed computer-human interfaces to achieve a clinically acceptable review time.

US 20090220139A1 describes a means for detecting a contour line that surrounds an object area of the mammogram, which is defined by an object.

"Computer-Aided Detection and Diagnosis of Breast Cancer With Mammography: Recent Advances", IEEE Transactions on Information Technology In Biomedicine, Vol. 13, No. 2, March 2009, pp. 236-251, describes detection of architectural distortion in mammograms. The paper describes using image processing techniques addressing bilateral asymmetry, by applying alignment of the left and right breast images before performing asymmetry analysis. The paper further describes using procedures to compare the corresponding anatomical regions between the left and right breast images in terms of shape, texture, and density. The paper also describes a technique for the detection of bilateral asymmetry that includes a semi-automated texture-based procedure for the segmentation of the glandular tissue and measures of shape and registration cost between views for the detection of asymmetry.

SUMMARY OF THE INVENTION

It would be advantageous to have an improved processing of a breast image. To better address this concern, a first aspect of the invention provides a system comprising a glandular tissue contour detector for detecting a contour of a glandular tissue represented in the breast image. It was found that the contour of the glandular tissue of a breast provides useful summary information about the breast architecture. Having this contour of the glandular tissue available allows comparing the breast architecture in different images more easily. Moreover, the shape of the contour may reveal irregularities that are relevant for a diagnosis.

The glandular tissue detector may be arranged for detecting the contour of a region within the image that comprises the mammary glands of a breast represented in the breast image.

The glandular tissue contour detector may comprise a concave hull determiner for determining a concave hull of the region to obtain the contour. Such a concave hull, as opposed to a convex hull, may reveal more details of the breast architecture that are relevant when comparing the contours of different breast images.

The system may comprise a display unit for displaying the breast image with the contour superimposed. This allows the assessment of the breast architecture by a user.

The display unit may be arranged for displaying a first breast image with the contour of the glandular tissue represented in the first breast image superimposed, and a second breast image with the contour of the glandular tissue represented in the second breast image superimposed. This allows for an easy comparison by a user of the breast architecture shown in the two breast images.

The first breast image and the second breast image may be displayed simultaneously one beside the other. This is an efficient arrangement for comparing the two contours, facilitating the assessment of differences between the contours in the images.

The first breast image and the second breast image may be displayed sequentially, preferably both breast images are displayed in the same display area and with the same orientation (nipples facing in the same direction). This is another visualization option that facilitates the assessment of differences between the contours of the images.

The system may comprise an aligner for panning and/or zooming the breast image to align the contour within a predetermined area of the display. This is based on the insight that a relevant reference for aligning the breast image is the glandular tissue. Consequently, reviewing the images is easier if the images are shown with the glandular tissue aligned. Moreover, by zooming in automatically on the glandular tissue, the images may be displayed with a relatively large zoom factor, while still showing the glandular tissue.

This may reduce the need to pan to other parts of the image for inspection with a high zoom factor.

The aligner may be arranged for vertically aligning the breast image to fit the contour within a predetermined horizontal strip of the display. This ensures that the user can expect the glandular tissue to be displayed at a specific height.

The display may comprise a first display area and a second display area, wherein the horizontal strip intersects both display areas, wherein a first breast image is displayed in the first display area and the second breast image is displayed in the second display area, and wherein the aligner is arranged for vertically aligning the first breast image to fit the contour of the glandular tissue represented in the first breast image within the horizontal strip, and vertically aligning the second breast image to fit the contour of the glandular tissue represented in the second breast image within the horizontal strip. This makes it easier to compare the two images.

The system may comprise a viewing parameter determiner for determining a viewing parameter for displaying the breast image, based on image content of a region of the breast image enclosed by the contour. This way, the viewing parameter is optimized for the region of the breast image showing the glandular tissue. This provides an optimized visualization of the glandular tissue.

The system may be implemented on a workstation.

In another aspect, the invention provides an imaging apparatus comprising the system according to the invention.

In another aspect, the invention provides a method of processing a breast image, comprising detecting a contour of a glandular tissue represented in the breast image. This may be performed by detecting the contour of a region within the image that comprises the mammary glands of a breast represented in the breast image.

In another aspect, the invention provides a computer program product comprising instructions arranged for causing a processor system to perform the method set forth.

It will be appreciated by those skilled in the art that two or more of the above-mentioned embodiments, implementations, and/or aspects of the invention may be combined in any way deemed useful. Moreover, the invention may be applied to two-dimensional, three-dimensional, or higher-dimensional image data. The image data may be obtained using any image acquisition modality, including X-ray, computed tomography, ultrasound, and magnetic resonance imaging.

Modifications and variations of the image acquisition apparatus, the workstation, the system, the method, and/or the computer program product, which correspond to the described modifications and variations of the system, can be carried out by a person skilled in the art on the basis of the present description.

BRIEF DESCRIPTION OF THE DRAWINGS

These and other aspects of the invention are apparent from and will be elucidated hereinafter with reference to the drawings. In the drawings, similar items have been marked with the same reference numerals.

DETAILED DESCRIPTION OF EMBODIMENTS

Figure 1:
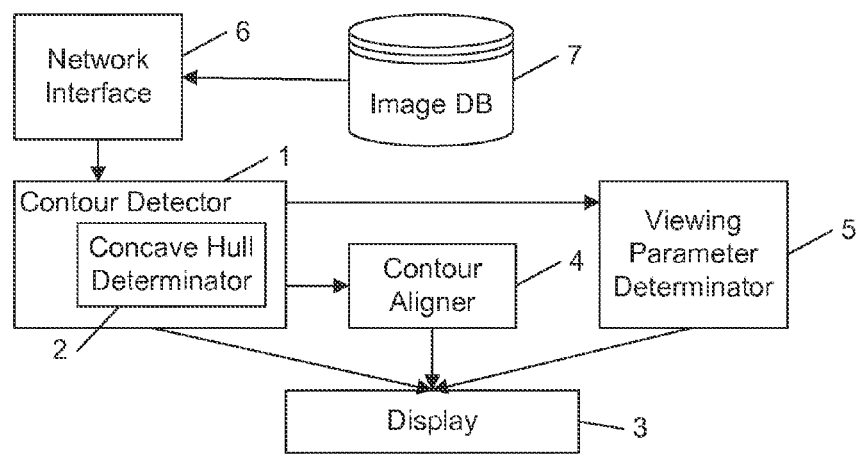
FIG. 1 is a block diagram of a system for processing and/or displaying a breast image.

FIG. 1 illustrates a system for processing a breast image. The system may be implemented in hardware, using dedicated electronic circuitry. Alternatively, the system may be implemented partly or completely by means of software. The software may be arranged to run on a workstation. It is also possible that the software is executed on a distributed computer system. The system may comprise user interface hardware, such as a mouse and/or keyboard and/or touch input device, for allowing a user to operate the system. The system may further comprise a display device, optionally a touch sensitive display device, for displaying images and a user interface. The system may further comprise a storage device and/or a network interface 6 to connect to an external database system 7. This allows the system to receive image data and/or store the results, such as computed contours, viewing parameters, and/or image alignment information.

As shown in the figure, the system may comprise a glandular tissue contour detector 1 arranged for processing the image to detect a contour 407 of a glandular tissue 303 represented in the breast image 310. The glandular tissue contour detector 1 may be arranged for receiving the breast image 310 from the network interface 6 or storage device. The contour may be detected as an outline of a region in the breast image 310 that predominantly shows mammary glands.

The glandular tissue contour detector 1 may be arranged for employing a suitable segmentation method to determine the region of the image corresponding to the glandular tissue. Such a segmentation method may involve an adaptive shape model. Adaptive shape models are known in the art per se. It is also possible to use feature detection, such as detecting local mean and standard deviation, or other local properties, to detect the glandular tissue.

The glandular tissue contour detector 1 may comprise a concave hull determiner 2 for determining a concave hull of the region to obtain the contour 407. This concave hull determiner 2 may be arranged for computing the contour by determining the boundary of the glandular tissue-comprising region. The concave hull determiner 2 may be arranged for determining the contour subject to a smoothness constraint.

The system may also comprise a display unit 3 arranged for displaying the breast image 310 with the contour 407 superimposed. This may be displayed using a display device, such as a computer monitor. Alternatively, another output device, such as a printer, in particular a film printer, may be used.

The system may be arranged for displaying two images, one beside the other. For example, the display unit 3 may be arranged for displaying a first breast image 310 with the contour 407 of the glandular tissue 303 represented in the first breast image 310 superimposed, and a second breast image 311 with the contour 408 of the glandular tissue 304 represented in the second breast image 311 superimposed. Accordingly, the input 6 and the glandular tissue contour detector 1 may be arranged to receive and process these two images just before displaying takes place. Typically, the input 6 will be arranged for retrieving two images of the same patient, for example a right breast image 310 and a left breast image 311. The input 6 may feed these two images to the glandular tissue contour detector 1 for performing the contour detection, after which the two images may be displayed by the display unit, for example in the format shown in FIG. 4.

It is also possible that the contour detection takes place in advance, and the contours are stored in the database 7, ready for being displayed by the display unit 3 at a later time.

The first breast image 310 and the second breast image 311 may be displayed simultaneously one beside the other. Preferably, the breast images 310 and 311 are displayed in a symmetrical arrangement, with the nipples facing away from each other.

The system may comprise an aligner 4 for panning and/or zooming the breast image 310. This alignment may be performed automatically based on the detected contour 407. The contour 407 may be aligned within a predetermined area of the display. The image may be panned and/or zoomed such that the contour just fits within the predetermined area of the display. The zoom factor employed may be the largest zoom factor that allows the contour to fit within the predetermined area of the display.

As an example, the aligner 4 may be arranged for vertically aligning the breast image 310 to fit the contour within a predetermined horizontal strip 520 of the display.

Figure 5:
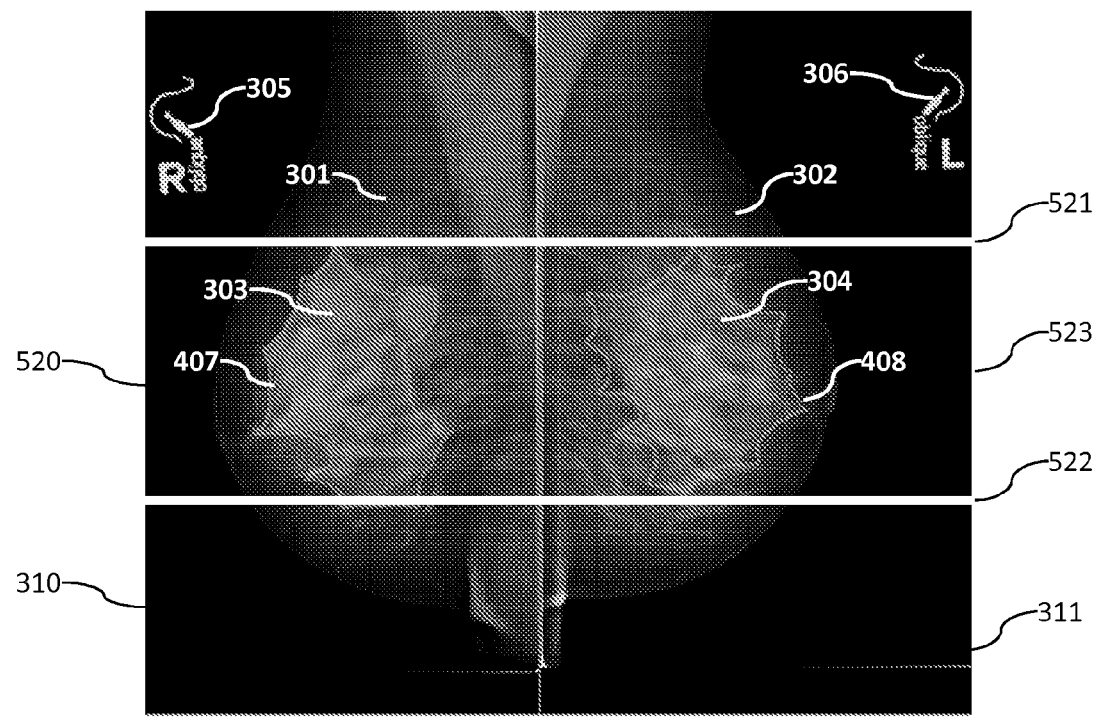
FIG. 5 shows a pair of breast images with a region for aligning the contours.

FIG. 5 illustrates a horizontal strip (from numeral 520 to numeral 523) of a display device, wherein the horizontal strip 520, 523 extends over two display areas of the display device on which breast images 310, 311 are shown. The top and bottom boundaries of the strip 520, 523 are indicated by means of the white lines 521 and 522, respectively. These white lines 521, 522 are reproduced in FIG. 5 to illustrate the concept. It is optional to display them during normal operation of the system. The images have been zoomed and panned in such a way that the contours just fit within the strip 520, 523.

To achieve such a result, a first display area and a second display area are allocated on the total display area of a display device. The horizontal strip 520, 523 intersects both display areas, wherein a first breast image 310 is displayed in the first display area and the second breast image 311 is displayed in the second display area. The aligner 4 is arranged for vertically aligning the first breast image 310 to fit the contour 407 of the glandular tissue 303 represented in the first breast image 310 within the horizontal strip 520, and vertically aligning the second breast image 311 to fit the contour 408 of the glandular tissue 304 represented in the second breast image 311 within the horizontal strip 523. This way, the contours of the two images are vertically aligned, making it easier to assess the symmetry of the breast architecture.

The aligned images may be displayed with the contours superimposed. However, this is optional.

The system may comprise a viewing parameter determiner 5 for determining a viewing parameter for displaying the breast image 310, based on image content of a region of the breast image enclosed by the contour 407. For example, the viewing parameter is at least one of: a contrast setting, a window width and/or window level setting, a parameter of an image enhancement algorithm. For example, the intensity levels of pixels of the image portion enclosed by the contour 407 is taken into account to determine the viewing parameter, whereas intensity levels of pixels outside that image portion are not taken into account.

The images with the contour superimposed may be stored in a storage system, such as the database 7. Alternatively, the contour may be stored as a separate data object. The image with the contour superimposed, or a symmetrically arranged pair of breast images with contours superimposed may also be included in a medical report.

Figure 2:
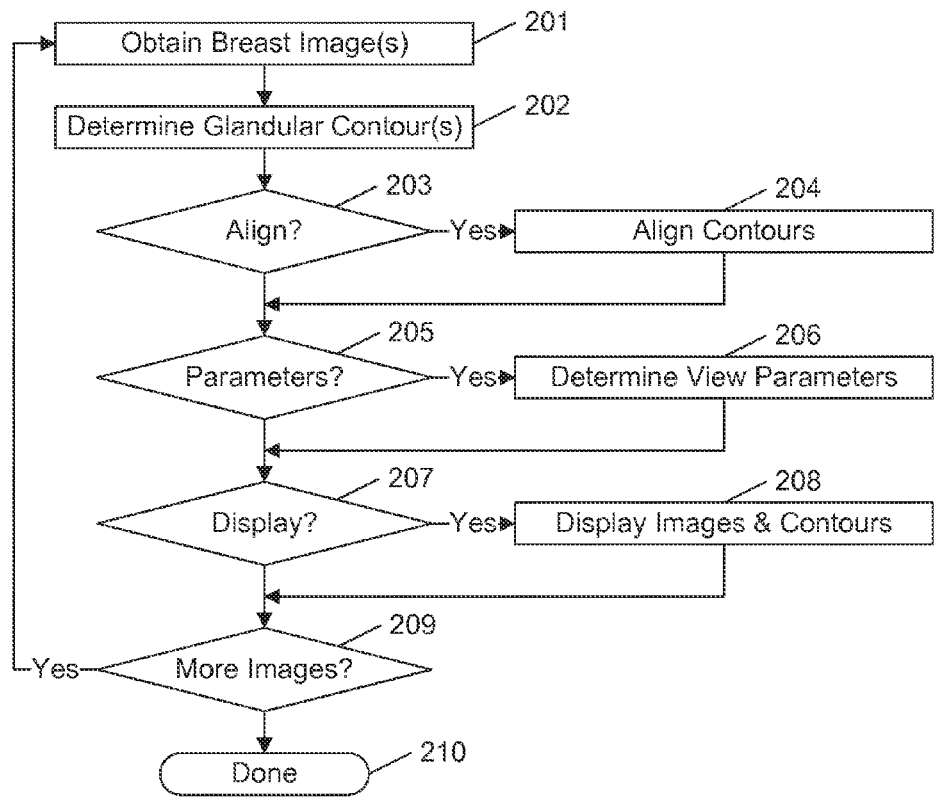
FIG. 2 is a flowchart of a method of processing and/or displaying a breast image.

FIG. 2 illustrates a method of processing and/or displaying one or more breast images. The method starts with step 201 of determining breast image(s) for which a contour needs to be determined. Next, in step 202, for each of the determined breast image(s), a contour 407 of a glandular tissue 303 represented in the breast image 310 is determined. In step 203, it is decided whether to align the images based on the contour 407. If so, in step 204 the images are aligned based on the contour detected in step 202. In step 205, it is decided whether the viewing parameters need to be determined. If so, in step 206, at least one viewing parameter is determined for at least one of the images, based on the region of the image enclosed by the contour. It is also possible to determine one or more viewing parameters based on the image content of the regions enclosed by the contours of a plurality of images determined in step 201. The same viewing parameters may thereafter be applied to the whole set of images, to improve consistency of image display. In step 207, it is decided whether the image(s) need to be displayed on a display device. If so, in step 208, the images are displayed, optionally with the contour(s) determined in step 202 superimposed, optionally using the alignment generated in step 204, optionally using the viewing parameter(s) determined in step 206. In step 209, it is decided whether more images need to be processed. If so, the method proceeds from step 201. Otherwise, the method terminates in step 210. The skilled person is able to modify the method as needed. The method may be implemented by means of a computer program.

Figure 3:
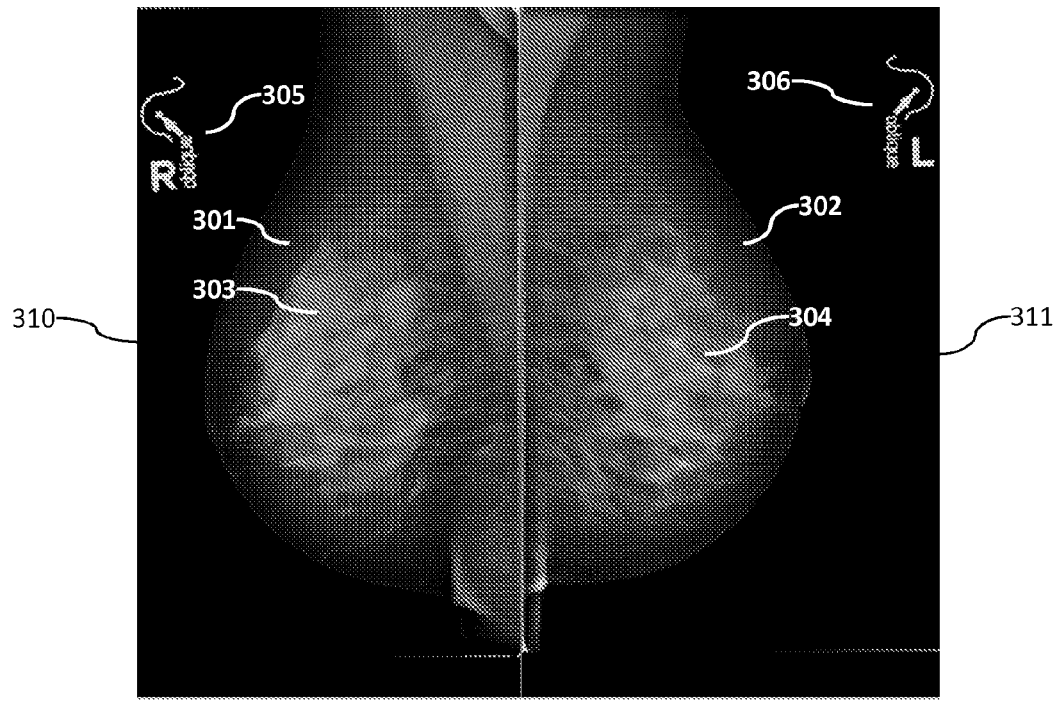
FIG. 3 shows a pair of breast images.

FIG. 3 shows a pair of MLO breast images, more particularly an image 310 of a right breast 301 and an image 311 of a left breast 302. The glandular tissue 303 of the right breast 301 and the glandular tissue 304 of the right breast 302 are clearly visible. The skin line may be hard to detect in the images. The images further comprise some annotation 305, 306. The annotation includes an R for right breast and an L for left breast.

Figure 4:
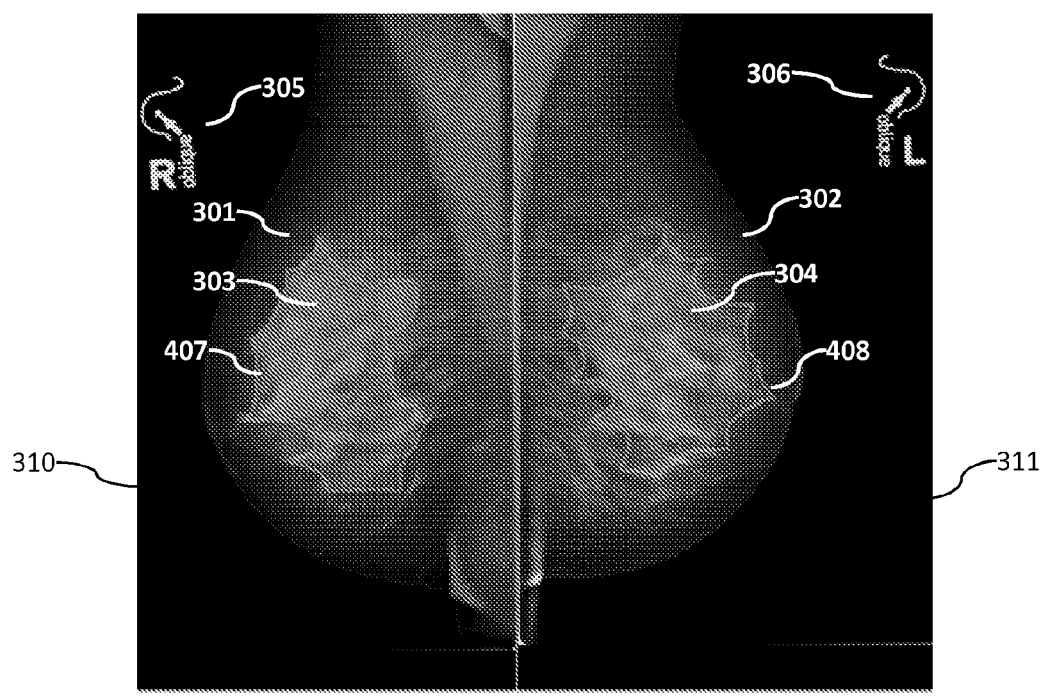
FIG. 4 shows a pair of breast images with a contour of a glandular tissue represented in the breast image superimposed.

FIG. 4 shows the same pair of MLO breast images, with a contour 407, 408 of the breast architecture drawn over each breast image 310, 311. A method for processing a breast image might comprise the following steps: Detection of glandular tissue, computing the convex hull of the glandular tissue, and superimposing the contour on the mammography image. The result of such a method is shown in FIG. 4.

FIG. 5 shows schematically how the right breast image 310 and the left breast image 311 can be aligned in such a way that the respective contours 407, 408 just fit within the designated horizontal strip 520,523 used as a vertical alignment region. In particular, the highest point of the each contour 407, 408 is located on the top boundary 521 of the horizontal strip 520, 523. The lowest point of each contour 407, 408 is located on the bottom boundary 522 of the horizontal strip 520,523.

Image characteristics within the glandular tissue region of an image may be summarized without regard to image characteristics of parts of the image outside the glandular tissue region (such as fat, muscle and/or skin).

A plurality of mammography images may be registered with respect to the breast architecture. This results in an improved display for prior and current exams or any other exam since the most important tissue is aligned for image comparison.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise calls to each other. An embodiment relating to a computer program product comprises computer-executable instructions corresponding to each processing step of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a storage medium, such as a ROM, for example, a CD ROM or a semiconductor ROM, or a magnetic recording medium, for example, a flash drive or a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for processing a breast image, comprising:
   a glandular tissue contour detector that detects a contour of a glandular tissue represented in the breast image, the glandular tissue contour detector cornprising a concave hull determiner that determines a concave hull of a region in the breast image comprising the mammary glands of a breast so as to obtain the contour; and
   a display unit that displays the breast image with the contour superimposed.

2. The system according to claim 1, wherein the glandular tissue detector is arranged that detects the contour of a region within the image that comprises the mammary glands of a breast represented in the breast image.

3. The system according to claim 1, wherein the display unit is arranged to display a first breast image with the contour of the glandular tissue represented in the first breast image superimposed, and a second breast image with the contour of the glandular tissue represented in the second breast image superimposed.

4. The system according to dam 3, wherein the first breast image and the second breast image are displayed concurrently.

5. The system according to claim 1, comprising an aligner to align the contour within a predetermined area of the display.

6. The system according to claim 5, wherein the aligner vertically aligns the breast image to fit the contour within a predetermined horizontal strip of the display.

7. The system according to claim 6, wherein the display comprises a first display area and a second display area, wherein the horizontal strip intersects both display areas, wherein a first breast image is displayed in the first display area and the second breast image is displayed in the second display area, and wherein the aligner vertically aligns the first breast image to fit the contour of the glandular tissue represented in the first breast image within the horizontal strip, and vertically aligns the second breast image to fit the contour of the glandular tissue represented in the second breast image within the horizontal strip.

8. The system according to claim 1, further comprising a viewing parameter determiner that determines a viewing parameter for displaying the breast image, based on image content of a region of the breast image enclosed by the contour.

9. A workstation comprising the system according to claim 1.

10. An imaging apparatus comprising the system according to claim 1.

11. A method of processing a breast image, comprising:
    detecting a contour of a glandular tissue represented in the breast image, including determining a concave hull of a region within the image that comprises the mammary glands of a breast represented in the breast image so as to obtain the contour; and
    displaying at least a portion of the breast image with the contour superimposed.

12. The method of claim 11, wherein the detecting includes detecting a first contour of a first breast image and a second contour of a second breast image, and the displaying includes concurrently displaying the first breast image with the first contour superimposed, and the second breast image with the second contour superimposed.

13. The method of claim 11, wherein the detecting includes detecting a first contour of a first breast image and a second contour of a second breast image, and the displaying includes sequentially displaying the first breast image with the first contour superimposed, and the second breast image with the second contour superimposed.

14. The method of claim 11, including vertically aligning the breast image to lit the contour within a predetermined area of the display.

15. The method of claim 11, wherein the displaying includes determining at least one viewing parameter for displaying the portion of the breast image based on image content of a region of the breast image enclosed by the contour.

16. A non-transitory computer-readable medium that includes a program that, when executed by a processor, causes the processor to:

obtain one or more breast images, analyze each breast image to determine a corresponding contour of a glandular tissue within the breast image, including determining a concave hull of a region within the image that comprises mammary glands; and provide a display of at least a portion of each breast image with the corresponding contour superimposed.

17. The medium of claim 16, wherein the one or more breast images includes a first breast image and a second breast image, and the display of the portion of each breast image with the corresponding contour is provided concurrently.

18. The medium of claim 16, wherein the one or more breast images includes a first breast image and a second breast image, and the display of the portion of each breast image with the corresponding contour is provided sequentially.

19. The medium of claim 16, wherein the program causes the processor to size the portion of each breast image on the display based on extents of at least one of the contours.

20. The system according to claim 3, wherein the first breast image and the second breast image are displayed sequentially.

\* \* \* \* \*